United States Patent [19]

Tayá et al.

[11] 4,202,825
[45] May 13, 1980

[54] QUERCETIN PENTAMETHYL CARBAMATE AND A PROCESS FOR ITS PREPARATION

[75] Inventors: Miguel M. Tayá; Dionisio M. Aedo; René Ricard, all of Barcelona, Spain

[73] Assignee: Rogador Sociedad Anonima, Esplugas de LLoebregat, Spain

[21] Appl. No.: 884,448

[22] Filed: Mar. 7, 1978

[30] Foreign Application Priority Data

Mar. 7, 1977 [ES] Spain .................................. 456.574

[51] Int. Cl.$^2$ .......................................... C07D 311/04
[52] U.S. Cl. .................................. 260/345.2; 424/283
[58] Field of Search ...................................... 260/345.2

[56] References Cited

U.S. PATENT DOCUMENTS

| 2,892,845 | 6/1959 | Jurd | 260/345.2 |
| 3,433,805 | 3/1969 | Krämer et al. | 260/345.2 |
| 3,468,913 | 9/1969 | Scharpf | 260/345.2 |
| 3,557,150 | 1/1971 | Drummond et al. | 260/345.2 |

FOREIGN PATENT DOCUMENTS 1409149 10/1975 United Kingdom .................. 260/345.2

OTHER PUBLICATIONS

Gabor, Symposia Angiologica Santoriana, 4th Int. Symp., Firbourg-Nyon, 1972, Angiologica 9: pp. 355–374 (1972).

*Primary Examiner*—Nicky Chan
*Attorney, Agent, or Firm*—Sughrue, Rothwell, Mion, Zinn and Macpeak

[57] ABSTRACT

A derivative of quercetin, quercetin pentamethyl carbamate, with therapeutical properties and a process for its preparation.

1 Claim, No Drawings

QUERCETIN PENTAMETHYL CARBAMATE AND A PROCESS FOR ITS PREPARATION

FIELD OF THE INVENTION

The present invention relates to a new compound, quercetin pentamethyl carbamate, having the structural formula:

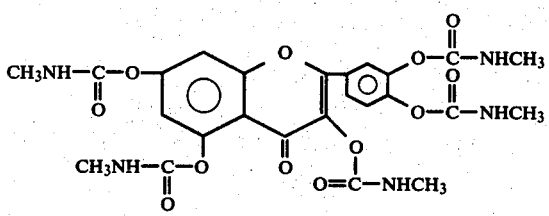

and to a process for the preparation thereof.

SUMMARY OF THE INVENTION

This new quercetin derivative has capillary protective and tonifying properties for the venous wall, which properties are of great interest for patients suffering from internal and external varicose veins of the legs, patients suffering from haemorrhoids, capillarites in diabetic retinitis, essential arterial hypertension, etc.

This compound, the chemical skeleton of which is quercetin, contains the free hydroxyls thereof protected by methylcarbamate radicals.

In this way there is obtained a product which retains the recognised vasoprotector action of the flavonoids, at the same time as it becomes very absorbable orally.

The invention, also relates to a process for the preparation of quercetin pentamethyl carbamate, wherein fundamentally quercetin having the structural formula:

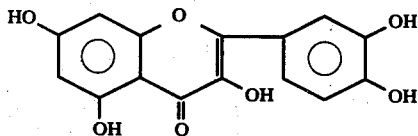

previously dissolved in anhydrous pyridine, is reacted with methyl isocyanate and dilute sulphuric acid is added to the resulting precipitate, which is stirred, filtered and washed to give quercetin pentamethyl carbamate.

To facilitate the understanding of the foregoing ideas, there is described hereinafter one example of the process according to the present invention. In view of its purely illustrative nature, this example must be deemed to be lacking in any limitative effect with respect to the scope of legal protection being applied for.

EXAMPLE

Quercetin (0.25 M, 75.5 g) is dissolved in 500 c.c. of anhydrous pyridine in a 1 liter capacity flask, having stirring and water bath means.

150 c.c. (2.5 M) of methyl isocyanate is added slowly with stirring, making sure that the flask does not heat up. Stirring is continued until the mass begins to solidify and it is allowed to rest for 4 hours at room temperature.

A thin layer chromatography test is performed to ensure that no free quercetin remains (Eluent: Benzene 90, methanol 10, acetic acid 4), developer: ferric chloride-methanol.

The mass is transferred to a 5 liter vessel equipped with stirring means and 3 liters of 7.5% sulphuric acid are added. Stirring is continued for 30 minutes, taking care to maintain an acid pH. The mixture is filtered and washed well with water to neutrality. Finally it is washed with cold methanol and dried.

113 grams of quercetin pentamethyl carbamate are obtained.

Melting point: 181° C.

Nitrogen: 11.9%.

Dissolved in methanol, the ultraviolet spectrum gives two maxima at 267 and 350 nm.

What we claim is:

1. Quercetin pentamethyl carbamate having the structural formula:

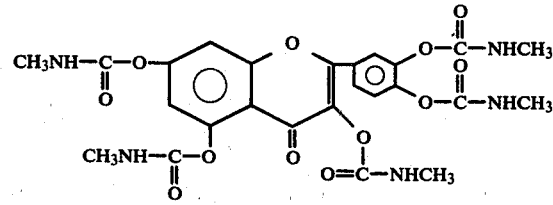

* * * * *

UNITED STATES PATENT AND TRADEMARK OFFICE
CERTIFICATE OF CORRECTION

PATENT NO. : 4,202,825
DATED : May 13, 1980
INVENTOR(S) : Taya et al.

It is certified that error appears in the above—identified patent and that said Letters Patent is hereby corrected as shown below:

On the title page,
column 1, Assignee, should be as follows:

[73] Assignee: Rocador Sociedad Anonima, Esplugas de Llobregat, Spain

Signed and Sealed this

Nineteenth Day of October 198.

[SEAL]

Attest:

Attesting Officer

GERALD J. MOSSINGHOFF

Commissioner of Patents and Trademarks